(12) United States Patent
Ravishankar et al.

(10) Patent No.: US 11,471,791 B2
(45) Date of Patent: *Oct. 18, 2022

(54) PROCESS FOR SEPARATING A HYDROPHIBIC MATERIAL FROM A MIXTURE OF HYDROPHOBIC AND HYDROPHILIC MATERIAL

(71) Applicant: HINDUSTAN PETROLEUM CORPORATION LIMITED, Mumbai (IN)

(72) Inventors: Raman Ravishankar, Bengaluru (IN); Chinthalapati Sivakesava Raju, Bengaluru (IN); Jitalaxmi Bharali, Bengaluru (IN); Sheshachala Srinivasa Narasimha, Bengaluru (IN); Peddy Venkat Chalapathi Rao, Bengaluru (IN); Nettem Venkateswarlu Choudary, Bengaluru (IN)

(73) Assignee: Hindustan Petroleum Corporation Limited, Mumbai (IN)

( * ) Notice: Subject to any disclaimer, the term of this patent is extended or adjusted under 35 U.S.C. 154(b) by 785 days.

This patent is subject to a terminal disclaimer.

(21) Appl. No.: 15/779,714

(22) PCT Filed: Nov. 8, 2016

(86) PCT No.: PCT/IN2016/050389
§ 371 (c)(1),
(2) Date: May 29, 2018

(87) PCT Pub. No.: WO2017/094023
PCT Pub. Date: Jun. 8, 2017

(65) Prior Publication Data
US 2020/0298144 A1 Sep. 24, 2020

(30) Foreign Application Priority Data
Nov. 30, 2015 (IN) .......................... 4503/MUM/2015

(51) Int. Cl.
| | | |
|---|---|---|
| B01D 17/04 | (2006.01) |
| B09C 1/08 | (2006.01) |
| C02F 1/68 | (2006.01) |
| C07C 233/47 | (2006.01) |
| C07C 323/59 | (2006.01) |
| E02B 15/04 | (2006.01) |
| E02B 15/10 | (2006.01) |
| C02F 101/32 | (2006.01) |
| C02F 103/00 | (2006.01) |
| C02F 103/08 | (2006.01) |

(52) U.S. Cl.
CPC .............. *B01D 17/047* (2013.01); *B09C 1/08* (2013.01); *C02F 1/682* (2013.01); *C07C 233/47* (2013.01); *C07C 323/59* (2013.01); *E02B 15/041* (2013.01); *E02B 15/10* (2013.01); *B09C 2101/00* (2013.01); *C02F 2101/32* (2013.01); *C02F 2103/007* (2013.01); *C02F 2103/08* (2013.01)

(58) Field of Classification Search
CPC ... C09K 3/32; C09K 8/32; C09K 8/36; B01D 17/047; B07C 1/08; C02F 1/682; C02F 2101/32; C02F 2103/007; C02F 2103/08; C07C 233/47; C07C 323/59; E02B 15/041; E02B 15/10; B09C 2101/00
USPC .............. 210/711, 708; 405/128.75; 507/119
See application file for complete search history.

(56) References Cited

U.S. PATENT DOCUMENTS

| | | | | |
|---|---|---|---|---|
| 10,343,144 | B2 * | 7/2019 | Ravishankar | B01J 20/28047 |
| 2012/0201863 | A1 * | 8/2012 | John | A23L 33/10 424/400 |
| 2015/0322348 | A1 * | 11/2015 | Dasgupta | C10G 1/045 208/401 |

OTHER PUBLICATIONS

Kar et al, the article "Organogelation and Hydrogelation of Low-molecular weight Amphiphilic Dipeptides: pH Responsiveness in Phase-Selective Gelation and Dye Removal," Langmuir, pp. 8639-8648 (Year: 2009).*
International Search Report, dated Feb. 8, 2017 (PCT/IN2016/050389).
Subhra Kanti Mandal et al; The striking influence of SWNT-COOH on self-assembled gelation, Chemical Communications—Chemcom., vol. 48, No. 12, Dec. 12, 2011 (Dec. 12, 2011), pp. 1814-1816, XP055249490, ISSN: 1359-7345, DOI: 10.1039/c2cc16567h.
Tanmoy Kar et al: Organogelation and Hydrogelation of Low-Molecular-Weight Amphiphilic Dipeptides: pH Responsiveness in Phase-Selective Gelation and Dye Removal, Langmuir, American Chemical Society, US, vol. 25, No. 15, Aug. 4, 2009 (Aug. 4, 2009), pp. 8639-8648, XP008142798, ISSN: 0743-7463, DOI: 10.1021/LA804235E [retrieved on Apr. 1, 2009]; Figure 1.
Swapni L R. Jadhav et al:Sugar-Derived Phase-Selective Molecular Gelators as Model Solidifiers for Oil Spills, Angewandte Chemie International Edition, vol. 49, No. 42, Jul. 15, 2010 (Jul. 15, 2010), pp. 7695-7698, XP055249272, DE ISSN: 1433-7851, DOI: 10.1002/anie.201002095.

* cited by examiner

*Primary Examiner* — Claire A Norris
(74) *Attorney, Agent, or Firm* — Robert L. Stearns; Dickinson Wright, PLLC

(57) ABSTRACT

A process is provided for separating hydrophobic material from a mixture of hydrophobic and hydrophilic material using peptide-based amphiphilic organogelators.

20 Claims, No Drawings

PROCESS FOR SEPARATING A HYDROPHIBIC MATERIAL FROM A MIXTURE OF HYDROPHOBIC AND HYDROPHILIC MATERIAL

BACKGROUND

I. Technical Field

The subject matter described herein in general relates to a process for separating hydrophobic material from a mixture of hydrophobic and hydrophilic material. The subject matter further relates to a process for containing oil spillage. A gelator solution comprising a peptide based compound can be added to the oil spill on a surface to form a gel comprising oil which can be removed easily from the surface. The gel can be heated to obtain the oil.

2. RELATED ART

Selective removal of oil from water is an important subject in environmental science and industries. For example, oil spill over in sea can often result in release of spilled oil in seawater. Hence, fast and efficient inhibition of oil diffusion and its removal is important. Rivers can also be contaminated by oil by release of wastewater from industry. The most widely used method currently for removing oil is using high performing adsorbents.

The separators and reflux drums in hydrocarbon industries function based on the difference in density between oil and water/seawater. This conventional method has limitation as it is inefficient and leads to either loss of crude oil and petroleum liquid products with water, the oil laden water is finally routed to sea after treatment in Effluent Treatment Plants (ETP). These facilities will not work effectively for heavier hydrocarbons and crude oils whose densities are nearer to water.

In case of oil spillage over sea water, as an oil weathers the density difference between oil and water decreases, because the oil density increases due to evaporation of lighter components and also as the oil gradually forms water-in-oil emulsion. These changes occur simultaneously during weathering and reduce the effectiveness of separation.

The current processes employed in industry for interphase separation are mostly based on density difference and are inefficient and reports of limitations such as high carry over in either phase. There are no reports on proven continuous process technology capabilities for separating spilled marine oil, oil recovery from ETP in refineries as well as recovery of crude oil from sludge that deposits in the storage tanks.

For separation of emulsified water in an emulsion in centrifugal separation, additional water clean-up volume is approximately two to five times and recovery of removed water from an emulsion is a concern owing to low skimmer effectiveness.

Hence most of the separation processes employed in the hydrocarbon industry has the potential to improve effective skimming time, recovery effectiveness and capacity, and disposal.

Therefore, effective oil and water separation in marine oil spill clean-up operations, crude oil recovery from sludge as well as efficient ETP operation is the need of the industry and is a critical technological development in hydrocarbon industry. Any inefficiency in separation and final disposal would also affect the aquatic life and environment adversely.

The past inventions highlights on methods for removing oil using high performing adsorbents, which should be hydrophobic and oleophilic, highly porous and light. Widely used adsorbents for oil include hydrophobic polymers such as polypropylene and porous polydimethylsiloxane (PDMS) or inorganic nanofibers with hydrophobic polymer coating. Prior work also discloses the application of silica nanoparticles coated by polydimethysiloxane (PDMS) thin film.

Prior literature has not yet disclosed the design and development of a proven process technology designed for separation of crude oil as well as refinery distillates from aqueous phase with the application of peptide-based gels.

SUMMARY

The present disclosure relates to a process for separating a hydrophobic material from a mixture of hydrophobic and hydrophilic material, said process comprising the steps of: (a) contacting a compound of Formula I:

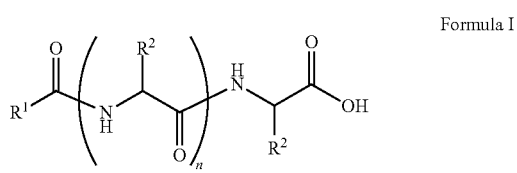

wherein, $R^1$ is substituted or unsubstituted $C_{10}$ to $C_{25}$ alkyl; $R^2$ is independently substituted $C_1$ to $C_{10}$ alkyl; n is 1 to 3, with an aromatic solvent at a temperature in the range of 40-90° C. to obtain a gelator solution; (b) contacting the gelator solution with a mixture of hydrophobic and hydrophilic material to obtain a gel comprising the hydrophobic material and a residue of hydrophilic material; (c) separating the gel from the residue of hydrophilic material; (d) heating the gel to a temperature in the range of 50-150° C. to obtain the hydrophobic material and to reclaim the compound of Formula I.

The present disclosure further relates to a process for separating a hydrophobic material from a mixture of hydrophobic and hydrophilic material, said process comprising the steps of: (a) contacting a compound of formula I:

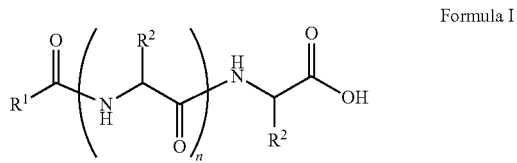

wherein, $R^1$ is substituted or unsubstituted $C_{10}$ to $C_{25}$ alkyl; $R^2$ is independently substituted $C_1$ to $C_{10}$ alkyl; n is 1 to 3, with a base and a hydrophilic solvent at a temperature in the range of 40-90° C. to obtain a polar gelator solution; (b) contacting the polar gelator solution with a mixture of hydrophobic and hydrophilic material to obtain a gel comprising the hydrophilic material and a residue of hydrophobic material; (c) separating the residue of hydrophobic material from the gel to obtain the hydrophobic material; and (d) heating the gel to a temperature in the range of 50-100° C. to reclaim the compound of Formula I.

The present disclosure relates to a process for separating a oil from a mixture of oil and water, said process comprising the steps of: (a) contacting a compound of formula I:

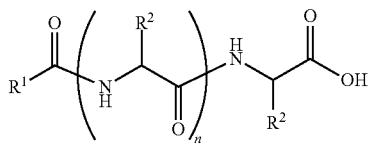

Formula I wherein, $R^1$ is substituted or unsubstituted $C_{10}$ to $C_{25}$ alkyl; $R^2$ is independently substituted $C_1$ to $C_{10}$ alkyl; n is 1 to 3, with toluene in a weight ratio of 1:99 at a temperature in the range of 60° C. to obtain a gelator solution; (b) contacting the gelator solution with a mixture of oil and water to obtain a gel and a residue of aqueous material; (c) separating the gel from the residue of aqueous material; and (d) heating the gel to a temperature in the range of 120° C. to obtain oil and to reclaim the compound of Formula I.

The present disclosure relates to a process for separating a oil from a mixture of oil and water, said process comprising the steps of: (a) contacting a compound of formula I:

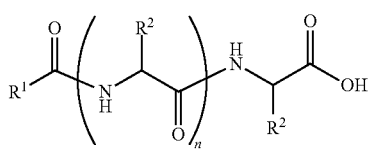

Formula I wherein, $R^1$ is substituted or unsubstituted $C_{10}$ to $C_{25}$ alkyl; $R^2$ is independently substituted $C_1$ to $C_{10}$ alkyl; n is 1 to 3, with toluene in a weight ratio of 1:99 at a temperature in the range of 60° C. to obtain a gelator solution; (b) contacting the gelator solution with a mixture of oil, water, and sludge to obtain a gel and a residue of aqueous material; (c) separating the gel from the residue of aqueous material; and (d) heating the gel to a temperature in the range of 120° C. to obtain oil and to reclaim the compound of Formula I.

The present disclosure relates to a process for separating oil from a mixture of oil and water, said process comprising the steps of: (a) contacting a compound of formula I:

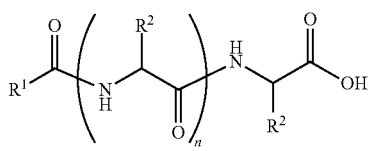

Formula I wherein, $R^1$ is substituted or unsubstituted $C_{10}$ to $C_{25}$ alkyl; $R^2$ is independently substituted $C_1$ to $C_{10}$ alkyl; n is 1 to 3, with sodium hydroxide and water at a temperature in the range of 60° C. to obtain a polar gelator solution; (b) contacting the polar gelator solution with a mixture of oil and water to obtain a gel and a residue of oil; (c) separating the residue of oil from the gel to obtain the oil; and (d) heating the gel to a temperature in the range of 70° C. to reclaim the compound of Formula I.

The present disclosure relates to a process of containing oil spillage, said process comprising the steps of: (a) contacting a compound of Formula I:

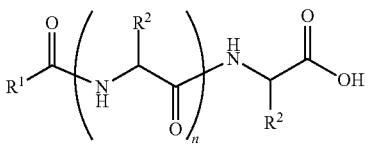

Formula I wherein, $R^1$ is substituted or unsubstituted $C_{10}$ to $C_{25}$ alkyl; $R^2$ is independently substituted $C_1$ to $C_{10}$ alkyl; n is 1 to 3, with an aromatic solvent at a temperature in the range of 40-90° C. to obtain a gelator solution; (b) contacting the gelator solution with spilled oil on a surface to obtain a gel comprising the oil on the surface, wherein the spilled oil is selected from the group of synthetic oil, natural oil, crude oil, fuel oil, petroleum fractions, combinations thereof; (c) gathering the gel from surface; (d) heating the gel to a temperature in the range of 50-150° C. to obtain the oil and to reclaim the compound of Formula I.

These and other features, aspects and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

DETAILED DESCRIPTION

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. Throughout this specification, unless the context requires otherwise the word "comprise", and variations, such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

The term "hydrocarbon(s)" refers to organic compounds that are made of hydrogen and carbon atoms. The source of the hydrocarbons may be from crude oils and refined petroleum products. Crude oil and other petroleum fractions may include compounds with hetero atoms like nitrogen, oxygen, sulfur, halogens and metallic elements along with hydrocarbons.

The term "gel" refers to a colloidal suspension of a solid dispersed in liquid and appear like semi solid.

The term "CRN" means Cracked Run Naptha (mainly comes from the Fluidized Catalytic Cracking (FCC) unit in the refinery).

The term "SRN" means Straight Run Naphtha, which comes from direct distillation of crude oil.

The term "diesel" means a specific fractional distillate of petroleum crude oil between 200° C. and 350° C. at atmospheric pressure.

The term "petroleum fractions" refers to "CRN", "SRN", and "diesel".

The terms "gelator solution" and "gelated solution" have been used interchangeably.

Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a temperature range of about 140° C. to about 180° C. should be interpreted to include not only the explicitly recited limits of about 140° C. to about 180° C., but also to include sub-ranges, such as 145° C. to 155° C., 150° C. to 170° C., and so forth, as well as individual amounts, including fractional amounts, within the specified ranges, such as 142.2° C., 140.6° C., and 141.3° C., for example.

The present disclosure relates to a process for separation of hydrophobic material from hydrophilic material, based on the operating principle of heating and cooling of the process stream. The separation is carried out by using amphiphilic gelators which exhibit a property of forming gel with either oil or water. The gelators have the potential for selective extraction of oil in water systems and water in oil systems.

In one implementation, the present disclosure relates to a process for separating a hydrophobic material from a mixture of hydrophobic and hydrophilic material, said process comprising the steps of: (a) contacting a compound of Formula I:

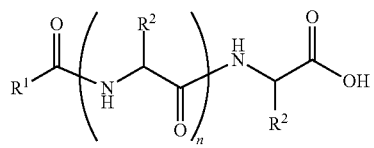

Formula I wherein, $R^1$ is substituted or unsubstituted $C_{10}$ to $C_{25}$ alkyl; $R^2$ is independently substituted $C_1$ to $C_{10}$ alkyl; n is 1 to 3, with an aromatic solvent at a temperature in the range of 40-90° C. to obtain a gelator solution; (b) contacting the gelator solution with a mixture of hydrophobic and hydrophilic material to obtain a gel comprising the hydrophobic material and a residue of hydrophilic material; (c) separating the gel from the residue of hydrophilic material; (d) heating the gel to a temperature in the range of 50-150° C. to obtain the hydrophobic material and to reclaim the compound of Formula I.

In one implementation, the present disclosure relates to a process for separating a hydrophobic material from a mixture of hydrophobic and hydrophilic material, said process comprising the steps of: (a) contacting a compound of Formula I:

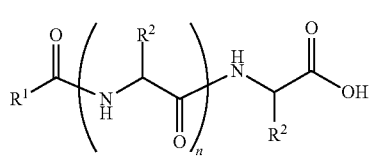

Formula I wherein, $R^1$ is unsubstituted $C_{10}$ to $C_{25}$ alkyl; $R^2$ is independently substituted $C_1$ to $C_{10}$ alkyl; and n is 1 to 3, with an aromatic solvent at a temperature in the range of 40-90° C. to obtain a gelator solution.

In one implementation, the present disclosure relates to a process for separating a hydrophobic material from a mixture of hydrophobic and hydrophilic material, said process comprising the steps of: (a) contacting a compound of Formula I:

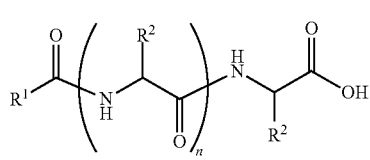

Formula I wherein, $R^1$ is unsubstituted $C_{13}$ to $C_{18}$ alkyl; $R^2$ is independently substituted $C_1$ to $C_{10}$ alkyl; and n is 1 to 3, with an aromatic solvent at a temperature in the range of 40-90° C. to obtain a gelator solution.

In one implementation, the present disclosure relates to a process for separating a hydrophobic material from a mixture of hydrophobic and hydrophilic material, said process comprising the steps of: (a) contacting a compound of Formula I:

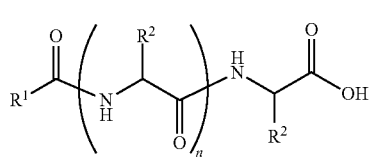

Formula I wherein, $R^1$ is unsubstituted $C_{15}$ alkyl; $R^2$ is independently substituted $C_1$ to $C_{10}$ alkyl; and n is 1 to 3, with an aromatic solvent at a temperature in the range of 40-90° C. to obtain a gelator solution.

In one implementation, the present disclosure relates to a process for separating a hydrophobic material from a mixture of hydrophobic and hydrophilic material, said process comprising the steps of: (a) contacting a compound of Formula I:

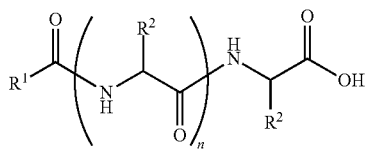

Formula I wherein, $R^1$ is substituted or unsubstituted $C_{10}$ to $C_{25}$ alkyl; wherein $R^2$ is $C_1$ to $C_{10}$ alkyl substituted with a heteroatom selected from O, N and S, wherein the heteroatom is substituted with $C_1$ to $C_3$ alkyl; and n is 1 to 3, with an aromatic solvent at a temperature in the range of 40-90° C. to obtain a gelator solution.

In one implementation, the present disclosure relates to a process for separating a hydrophobic material from a mixture of hydrophobic and hydrophilic material, said process comprising the steps of: (a) contacting a compound of Formula I:

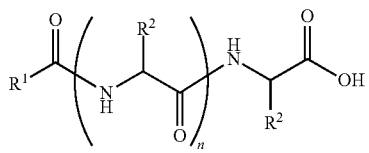

Formula I wherein, $R^1$ is unsubstituted $C_{10}$ to $C_{25}$ alkyl; wherein $R^2$ is $C_1$ to $C_{10}$ alkyl substituted with a heteroatom selected from O, N and S, wherein the heteroatom is substituted with $C_1$ to $C_3$ alkyl; and n is 1 to 3, with an aromatic solvent at a temperature in the range of 40-90° C. to obtain a gelator solution.

In one implementation, the present disclosure relates to a process for separating a hydrophobic material from a mixture of hydrophobic and hydrophilic material, said process comprising the steps of: (a) contacting a compound of Formula I:

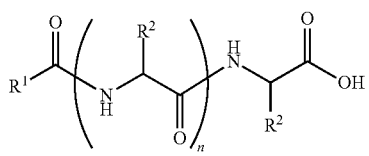

Formula I wherein, $R^1$ is unsubstituted $C_{13}$ to $C_{18}$ alkyl; wherein $R^2$ is $C_1$ to $C_{10}$ alkyl substituted with a heteroatom selected from O, N and S, wherein the heteroatom is substituted with $C_1$ to $C_3$ alkyl; and n is 1 to 3, with an aromatic solvent at a temperature in the range of 40-90° C. to obtain a gelator solution.

In one implementation, the present disclosure relates to a process for separating a hydrophobic material from a mixture of hydrophobic and hydrophilic material, said process comprising the steps of: (a) contacting a compound of Formula I:

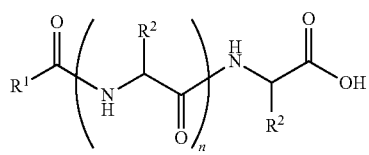

Formula I wherein, $R^1$ is unsubstituted $C_{15}$ alkyl; wherein $R^2$ is $C_1$ to $C_{10}$ alkyl substituted with a heteroatom selected from O, N and S, wherein the heteroatom is substituted with $C_1$ to $C_3$ alkyl; and n is 1 to 3, with an aromatic solvent at a temperature in the range of 40-90° C. to obtain a gelator solution.

In one implementation, the present disclosure relates to a process for separating a hydrophobic material from a mixture of hydrophobic and hydrophilic material, said process comprising the steps of: (al contacting a compound of Formula I:

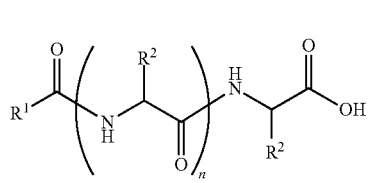

Formula I wherein, $R^1$ is substituted or unsubstituted $C_{10}$ to $C_{25}$ alkyl; wherein $R^2$ is $C_1$ to $C_5$ alkyl substituted with S which is further substituted with $C_1$ to $C_3$ alkyl; and n is 1 to 3, with an aromatic solvent at a temperature in the range of 40-90° C. to obtain a gelator solution.

In one implementation, the present disclosure relates to a process for separating a hydrophobic material from a mixture of hydrophobic and hydrophilic material, said process comprising the steps: (a) contacting a compound of Formula I:

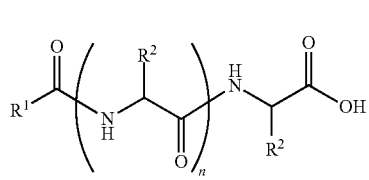

Formula I wherein, $R^1$ is unsubstituted $C_{10}$ to $C_{25}$ alkyl; wherein $R^2$ is $C_1$ to $C_5$ alkyl substituted with S which is further substituted with $C_1$ to $C_3$ alkyl; and n is 1 to 3, with an aromatic solvent at a temperature in the range of 40-90° C. to obtain a gelator solution.

In one implementation, the present disclosure relates to a process for separating a hydrophobic material from a mixture of hydrophobic and hydrophilic material, said process comprising the steps of: (a) contacting a compound of Formula I:

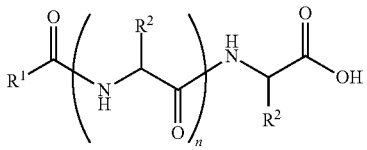

Formula I wherein, R¹ is unsubstituted $C_{13}$ to $C_{18}$ alkyl; wherein R² is $C_1$ to $C_5$ alkyl substituted with S which is further substituted with $C_1$ to $C_3$ alkyl; and n is 1 to 3, with an aromatic solvent at a temperature in the range of 40-90° C. to obtain a gelator solution.

In one implementation, the present disclosure relates to a process for separating a hydrophobic material from a mixture of hydrophobic and hydrophilic material, said process comprising the steps of: (a) contacting a compound of Formula I:

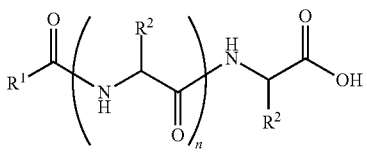

Formula I wherein, R¹ is unsubstituted $C_{15}$ alkyl; wherein R² is $C_1$ to $C_5$ alkyl substituted with S which is further substituted with $C_1$ to $C_3$ alkyl; and n is 1 to 3, with an aromatic solvent at a temperature in the range of 40-90° C. to obtain a gelator solution.

In yet another implementation, the present disclosure relates to a compound having the Formula:

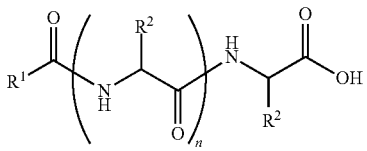

Formula I wherein, R¹ is unsubstituted $C_{13}$ to $C_{18}$ alkyl, R² is $C_1$ to $C_5$ alkyl substituted with S which is further substituted with $C_1$ to $C_3$ alkyl; and n is 1 to 3, with an aromatic solvent at a temperature in the range of 40-90° C. to obtain a gelator solution.

In one implementation, the present disclosure relates to a process for separating a hydrophobic material from a mixture of hydrophobic and hydrophilic material, said process comprising the steps of: (a) contacting a compound of Formula I:

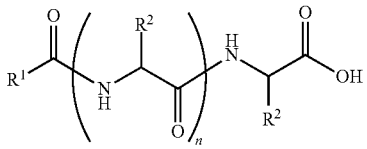

Formula I wherein, R¹ is substituted or unsubstituted $C_{10}$ to $C_{25}$ alkyl; wherein R² is $C_1$ to $C_5$ alkyl substituted with S which is further substituted with $C_1$ to $C_3$ alkyl; and n is 1 to 2, with an aromatic solvent at a temperature in the range of 40-90° C. to obtain a gelator solution.

In one implementation, the present disclosure relates to a process for separating a hydrophobic material from a mixture of hydrophobic and hydrophilic material, said process comprising the steps of: (a) contacting a compound of Formula I:

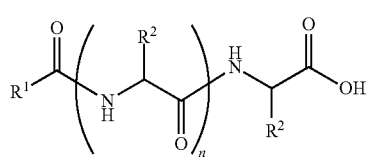

Formula I wherein, R¹ is unsubstituted $C_{10}$ to $C_{25}$ alkyl; wherein R² is $C_1$ to $C_5$ alkyl substituted with S which is further substituted with $C_1$ to $C_3$ alkyl; and n is 1 to 2, with an aromatic solvent at a temperature in the range of 40-90° C. to obtain a gelator solution.

In one implementation, the present disclosure relates to a process for separating a hydrophobic material from a mixture of hydrophobic and hydrophilic material, said process comprising the steps of: (a) contacting a compound of Formula I:

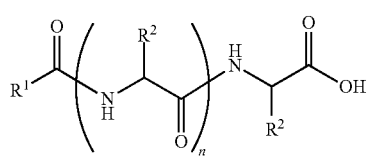

Formula I wherein, R¹ is unsubstituted $C_{13}$ to $C_{18}$ alkyl; wherein R² is $C_1$ to $C_5$ alkyl substituted with S which is further substituted with $C_1$ to $C_3$ alkyl; and n is 1 to 2, with an aromatic solvent at a temperature in the range of 40-90° C. to obtain a gelator solution.

In one implementation, the present disclosure relates to a process for separating a hydrophobic material from a mixture of hydrophobic and hydrophilic material, said process comprising the steps of: (a) contacting a compound of Formula I:

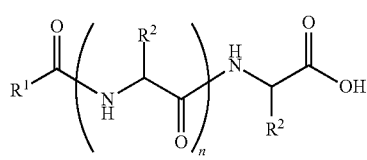

Formula I wherein, R¹ is unsubstituted $C_{15}$ alkyl; wherein R² is $C_1$ to $C_5$ alkyl substituted with S which is further substituted with $C_1$ to $C_3$ alkyl; and n is 1 to 2, with an aromatic solvent at a temperature in the range of 40-90° C. to obtain a gelator solution.

In one implementation, the present disclosure relates to a process for separating a hydrophobic material from a mixture of hydrophobic and hydrophilic material, said process comprising the steps of: (a) contacting a compound of Formula I:

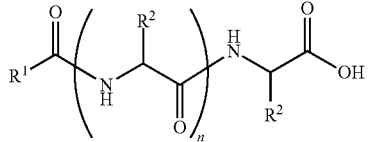

Formula I wherein, $R^1$ is unsubstituted $C_{13}$ to $C_{18}$ alkyl, $R^2$ is $C_1$ to $C_5$ alkyl substituted with S which is further substituted with $C_1$ to $C_3$ alkyl; and n is 1 to 2, with an aromatic solvent at a temperature in the range of 40-90° C. to obtain a gelator solution.

In one implementation, the present disclosure relates to a process for separating a hydrophobic material from a mixture of hydrophobic and hydrophilic material, said process comprising the steps of: (a) contacting a compound of Formula I:

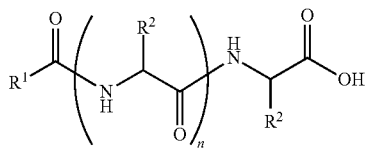

Formula I wherein, $R^1$ is substituted or unsubstituted $C_{10}$ to $C_{25}$ alkyl; wherein $R^2$ is $C_1$ to $C_5$ alkyl substituted with S which is further substituted with $C_1$ to $C_3$ alkyl; and n is 1, with an aromatic solvent at a temperature in the range of 40-90° C. to obtain a gelator solution.

In one implementation, the present disclosure relates to a process for separating a hydrophobic material from a mixture of hydrophobic and hydrophilic material, said process comprising the steps of: (a) contacting a compound of Formula I:

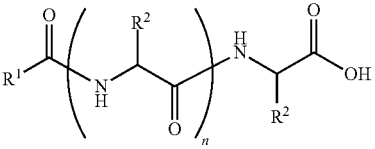

Formula I wherein, $R^1$ is unsubstituted $C_{10}$ to $C_{25}$ alkyl; wherein $R^2$ is $C_1$ to $C_5$ alkyl substituted with S which is further substituted with $C_1$ to $C_3$ alkyl; and n is 1, with an aromatic solvent at a temperature in the range of 40-90° C. to obtain a gelator solution.

In one implementation, the present disclosure relates to a process for separating a hydrophobic material from a mixture of hydrophobic and hydrophilic material, said process comprising the steps of: (a) contacting a compound of Formula I:

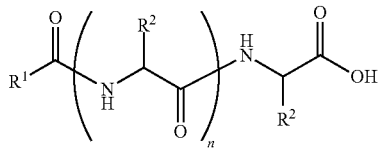

Formula I wherein, $R^1$ is unsubstituted $C_{13}$ to $C_{18}$ alkyl; wherein $R^2$ is $C_1$ to $C_5$ alkyl substituted with S which is further substituted with $C_1$ to $C_3$ alkyl; and n is 1, with an aromatic solvent at a temperature in the range of 40-90° C. to obtain a gelator solution.

In one implementation, the present disclosure relates to a process for separating a hydrophobic material from a mixture of hydrophobic and hydrophilic material, said process comprising the steps of: (a) contacting a compound of Formula I:

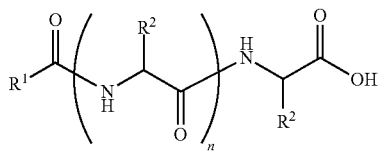

Formula I wherein, $R^1$ is unsubstituted $C_{15}$ alkyl; wherein $R^2$ is $C_1$ to $C_5$ alkyl substituted with S which is further substituted with $C_1$ to $C_3$ alkyl; and n is 1, with an aromatic solvent at a temperature in the range of 40-90° C. to obtain a gelator solution.

In one implementation, the present disclosure relates to a process for separating a hydrophobic material from a mixture of hydrophobic and hydrophilic material, said process comprising the steps of: (a) contacting a compound of Formula II with an aromatic solvent at a temperature in the range of 40-90° C. to obtain a gelator solution:

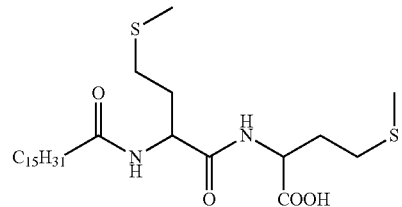

Formula II

The IUPAC name of the compound of Formula II is 4-(methylthio)-2-(4-(methylthio)-2-palmitamidobutanamido) butanoic acid.

In one implementation, the present disclosure relates to a process for separating a hydrophobic material from a mixture of hydrophobic and hydrophilic material, wherein the hydrophobic material is a hydrocarbon. In another implementation, the hydrophobic material is oil. Oil can be selected from the group consisting of SRN, CRN, diesel, crude oil, vegetable oil, and combinations thereof. In yet another implementation, oil can be selected from the group of synthetic oil, natural oil, crude oil, fuel oil, petroleum fractions, combinations thereof.

In a convention ETP process, different effluents such as spent caustic, water from oily water sewer etc. are initially routed to large oil catcher sump tank to remove the oil/distillates floating in the effluent stream. The oil floating effluent stream is further skimmed off/removed in the clarifier tank. However due to inefficient separation process, the treated stream is discharged to sea water with oil spill over. The process disclosed herein can efficiently remove oil from effluents.

In one implementation, the present disclosure relates to a process for separating a hydrophobic material from a mixture of hydrophobic and hydrophilic material, wherein the hydrophilic material is selected from the group consisting of water, polar solvents, sludge, and combinations thereof. In one implementation, the hydrophilic material is water. In one implementation, the hydrophilic material is water and sludge.

In one implementation, the present disclosure relates to a process for separating a hydrophobic material from a mixture of hydrophobic and hydrophilic material, wherein the mixture of hydrophobic and hydrophilic material is a biphasic mixture, wherein the biphasic mixture comprises of oil and water.

In one implementation, the present disclosure relates to a process for separating a hydrophobic material from a mixture of hydrophobic and hydrophilic material, wherein the mixture of hydrophobic and hydrophilic material is a triphasic mixture, wherein the triphasic mixture comprises of oil, water, and sludge.

In one implementation, the present disclosure relates to a process for separating a hydrophobic material from a mixture of hydrophobic and hydrophilic material, said process comprising the steps of contacting a compound of Formula I with an aromatic solvent to obtain a gelator solution, wherein the aromatic solvent is selected from the group consisting of toluene, xylene, ethylbenzene, petroleum fractions, and combinations thereof. In another implementation, the aromatic solvent is toluene.

In one implementation, the compound of Formula I is contacted with an aromatic solvent at a temperature in the range of 40-90° C. to obtain a gelator solution. In one implementation, the compound of Formula I is contacted with an aromatic solvent at a temperature in the range of 50-90° C. to obtain a gelator solution. In one implementation, the compound of Formula I is contacted with an aromatic solvent at a temperature in the range of 60° C.

In one implementation, the present disclosure relates to a process for separating a hydrophobic material from a mixture of hydrophobic and hydrophilic material, wherein the compound of Formula I weight % in the gelator solution is in the range of 0.1-20%. wherein the compound of Formula I weight % in the gelator solution is in the range of 0.1-20%. In another implementation, the present disclosure relates to a process for separating a hydrophobic material from a mixture of hydrophobic and hydrophilic material, wherein the compound of Formula I weight % in the gelator solution is in the range of 1-20%. In yet another implementation, the present disclosure relates to a process for separating a hydrophobic material from a mixture of hydrophobic and hydrophilic material, wherein the compound of Formula I weight % in the gelator solution is in the range of 1-10%.

The gelator solution can be contacted with the mixture of hydrophobic and hydrophilic material. As a result of this, a gel comprising the hydrophobic material is formed. To determine whether or not the addition amount of the gelator solution is sufficient for gel formation, a part of the gelator solution may be suspended in the mixture of hydrophobic and hydrophilic material and observing whether or not the hydrophobic material floats on the hydrophilic material surface. Specifically, when the hydrophobic material floats on the hydrophilic material, the amount of gelator solution is insufficient, and it is necessary to increase the amount of solution added. Conversely, when the hydrophobic material does not float on hydrophilic material, it indicates that the required amount of gelator has been mixed.

In one implementation, the gelator solution can be sprayed over the mixture of hydrophobic and hydrophilic material. The spraying can done by dispersion nozzles at a velocity of 2-20 m/sec.

In one implementation, the present disclosure relates to a process for separating a hydrophobic material from a mixture of hydrophobic and hydrophilic material, wherein the gelator solution forms a gel with the hydrophobic material. The gelator solution comprises the compound of Formula I and the aromatic solvent, wherein the compound of Formula I has an intrinsic property of forming a rigid or semi-rigid structure with the hydrophobic material; the rigid or semi-rigid structure being the gel.

In one implementation, the gel comprises the gelator solution and the hydrophobic material and the residue contains the hydrophilic material. In one implementation, the gel is separated from the residue of the hydrophilic material.

In one implementation, the present disclosure relates to a process for separating a hydrophobic material from a mixture of hydrophobic and hydrophilic material, wherein the gel is heated to a temperature 50-150° C. to obtain the hydrophobic material. In one implementation, the gel is heated to a temperature 50-100° C. to obtain the hydrophobic material. In one implementation, the gel is heated to a temperature 60-120° C. to obtain the hydrophobic material.

In one implementation, the hydrophobic material is obtained from the gel by distillation. In one implementation, the distillation is carried out in under reduced pressure.

In one implementation, the present disclosure relates to a process for separating a hydrophobic material from a mixture of hydrophobic and hydrophilic material, heating of the gel yields the hydrophobic material and the gelator solution. The aromatic solvent in the gelator solution evaporates, leaving behind the compound of Formula I. The compound of formula I is reclaimed and reused again. In one implementation, the compound of Formula I retains 99% activity.

In one implementation, the present disclosure relates to a process for separating a oil from a mixture of oil and water, said process comprising the steps of: (a) contacting a compound of formula I:

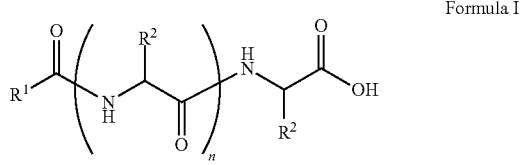

Formula I wherein, $R^1$ is substituted or unsubstituted $C_{10}$ to $C_{25}$ alkyl; $R^2$ is independently substituted $C_1$ to $C_{10}$ alkyl; n is 1 to 3, with toluene in a weight ratio of 1:99 at a temperature in the range of 60° C. to obtain a gelator solution; (b) contacting the gelator solution with a mixture of oil and water to obtain a gel and a residue of aqueous material; (c) separating the gel from the residue of aqueous material; and (d) heating the gel to a temperature in the range of 120° C. to obtain oil and to reclaim the compound of Formula I.

In one implementation, the present disclosure relates to a process for separating a oil from a mixture of oil and water, said process comprising the steps of: (a) contacting a compound of Formula II with toluene in a weight ratio of 1:99 at a temperature in the range of 60° C. to obtain a gelator solution; (b) contacting the gelator solution with a mixture of oil and water to obtain a gel and a residue of aqueous material; (c) separating the gel from the residue of aqueous material; and (d) heating the gel to a temperature in the range of 120° C. to obtain oil and to reclaim the compound of Formula II.

In one implementation, the present disclosure relates to a process for separating a oil from a mixture of oil and water, said process comprising the steps of: (a) contacting a compound of formula I:

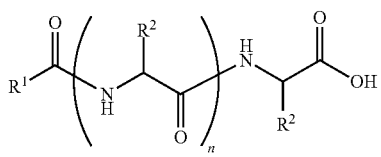

Formula I wherein, $R^1$ is substituted or unsubstituted $C_{10}$ to $C_{25}$ alkyl; $R^2$ is independently substituted $C_1$ to $C_{10}$ alkyl; n is 1 to 3, with toluene in a weight ratio of 1:99 at a temperature in the range of 60° C. to obtain a gelator solution; (b) contacting the gelator solution with a mixture of oil, water, and sludge to obtain a gel and a residue of aqueous material; (c) separating the gel from the residue of aqueous material; and (d) heating the gel to a temperature in the range of 120° C. to obtain oil and to reclaim the compound of Formula I.

In one implementation, the present disclosure relates to a process for separating a hydrophobic material from a mixture of hydrophobic and hydrophilic material, said process comprising the steps of: (a) contacting a compound of formula I:

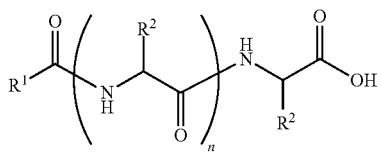

Formula I wherein, $R^1$ is substituted or unsubstituted $C_{10}$ to $C_{25}$ alkyl; $R^2$ is independently substituted $C_1$ to $C_{10}$ alkyl; n is 1 to 3, with a base and hydrophilic solvent at a temperature in the range of 40-90° C. to obtain a polar gelator solution; (b) contacting the polar gelator solution with a mixture of hydrophobic and hydrophilic material to obtain a gel comprising the hydrophilic material and a residue of hydrophobic material; (c) separating the residue of hydrophobic material from the gel to obtain the hydrophobic material; and (d) heating the gel to a temperature in the range of 50-100° C. to reclaim the compound of Formula I.

In one implementation, the present disclosure relates to a process for separating a hydrophobic material from a mixture of hydrophobic and hydrophilic material, said process comprising the steps of: (a) contacting a compound of Formula II with a base and hydrophilic solvent at a temperature in the range of 40-90° C. to obtain a polar gelator solution; (b) contacting the polar gelator solution with a mixture of hydrophobic and hydrophilic material to obtain a gel comprising the hydrophilic material and a residue of hydrophobic material; (c) separating the residue of hydrophobic material from the gel to obtain the hydrophobic material; and (d) heating the gel to a temperature in the range of 50-100° C. to reclaim the compound of Formula II.

The polar gelator solution can be contacted with the mixture of hydrophobic and hydrophilic material. As a result of this, a gel comprising the hydrophilic material is formed.

In one implementation, the present disclosure relates to a process for separating a hydrophobic material from a mixture of hydrophobic and hydrophilic material, wherein the hydrophobic material is a hydrocarbon. In another implementation, the hydrophobic material is oil. Oil can be selected from the group consisting of SRN, CRN, diesel, crude oil, vegetable oil, and combinations thereof. In one implementation, the hydrophobic material can be oil selected from the group of synthetic oil, natural oil, crude oil, fuel oil, petroleum fractions, combinations thereof.

In one implementation, the present disclosure relates to a process for separating a hydrophobic material from a mixture of hydrophobic and hydrophilic material, wherein the hydrophilic material is selected from the group consisting of water, polar solvents, sludge, and combinations thereof. In one implementation, the hydrophilic material is water. In one implementation, the hydrophilic material is water and sludge.

In one implementation, the present disclosure relates to a process for separating a hydrophobic material from a mixture of hydrophobic and hydrophilic material, wherein the mixture of hydrophobic and hydrophilic material is a biphasic mixture, wherein the biphasic mixture comprises of oil and water.

In one implementation, the present disclosure relates to a process for separating a hydrophobic material from a mixture of hydrophobic and hydrophilic material, said process comprising the steps of: contacting a compound of Formula I with a base and a hydrophilic solvent to obtain a gelator solution, wherein the base is selected from the group consisting of sodium hydroxide, potassium hydroxide, and combinations thereof. In another implementation, the base is sodium hydroxide. In yet another implementation, the base can be inorganic or organic base.

In one implementation, the compound of Formula I or II is contacted with a base and a hydrophilic solvent at a temperature in the range of 40-90° C. In one implementation, the compound of Formula I is contacted with a base and a hydrophilic solvent at a temperature in the range of 45-75° C. In one implementation, the compound of Formula I or II is contacted with a base and a hydrophilic solvent at a temperature in the range of 60° C. The hydrophilic solvent can be water.

In one implementation, the present disclosure relates to a process for separating a hydrophobic material from a mixture of hydrophobic and hydrophilic material wherein the polar gelator solution is contacted with a mixture of hydrophobic and hydrophilic material to obtain a gel comprising the hydrophilic material and a residue of hydrophobic material. In one implementation, the compound of Formula I or II weight % in the polar gelator solution is in the range of 0.1-20%. In one implementation, the compound of Formula I or II weight % in the polar gelator solution is in the range of 1-20%. In another implementation, the compound of Formula I weight % in the polar gelator solution is in the range of 1-10% In one implementation, the present disclosure relates to a process for separating a hydrophobic material from a mixture of hydrophobic and hydrophilic material, wherein the polar gelator solution forms a gel with the hydrophilic material. The gelator solution comprises the salt of compound of Formula I, wherein the salt of Formula I has an intrinsic property of forming a rigid or semi-rigid structure with the hydrophilic material; the rigid or semi-rigid structure being the gel. Contacting the compound of Formula I with base results in the formation of a salt of the compound of formula I which is hydrophilic.

In one implementation, the gel comprises the gelator solution and the hydrophilic material and the residue contains the hydrophobic material. In one implementation, the residue of hydrophobic material is separated from the gel to obtain the hydrophobic material.

In one implementation, the present disclosure relates to a process for separating a hydrophobic material from a mixture of hydrophobic and hydrophilic material, wherein the gel comprising the hydrophilic material is heated to a temperature 50-100° C. to reclaim the compound of Formula I or II. In one implementation, the gel comprising the hydrophilic material is heated to a temperature 60-80° C. to reclaim the compound of Formula I or II. The reclaimed compound of Formula I or II is reused again. In one implementation, the compound of Formula I or II retains 99% activity.

In one implementation, the present disclosure relates to a process for separating oil from a mixture of oil and water, said process comprising the steps of: (a) contacting a compound of Formula I:

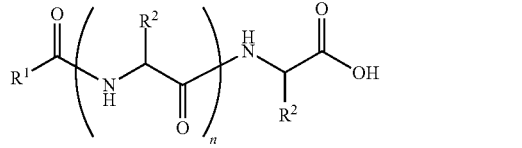

Formula I wherein, $R^1$ is substituted or unsubstituted $C_{10}$ to $C_{25}$ alkyl; $R^2$ is independently substituted $C_1$ to $C_{10}$ alkyl; n is 1 to 3, with sodium hydroxide and water at a temperature in the range of 60° C. to obtain a gelator solution; (b) contacting the gelator solution with a mixture of oil and water to obtain a gel and a residue of oil; (c) separating the residue of oil from the gel to obtain the oil; and (d) heating the gel to a temperature in the range of 70° C. to reclaim the compound of Formula I.

In one implementation, the present disclosure relates to a process for separating oil from a mixture of oil and water, said process comprising the steps of: (a) contacting a compound of Formula II with sodium hydroxide and water at a temperature in the range of 60° C. to obtain a gelator solution; (b) contacting the gelator solution with a mixture of oil and water to obtain a gel and a residue of oil; (c) separating the residue of oil from the gel to obtain the oil; and (d) heating the gel to a temperature in the range of 70° C. to reclaim the compound of Formula II.

In one implementation, the present disclosure relates to a process of containing oil spillage, said process comprising the steps of: contacting a compound of Formula I:

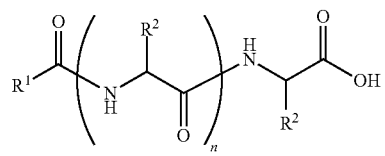

Formula I wherein, $R^1$ is substituted or unsubstituted $C_{10}$ to $C_{25}$ alkyl; $R^2$ is independently substituted $C_1$ to $C_{10}$ alkyl; n is 1 to 3, with an aromatic solvent at a temperature in the range of 40-90° C. to obtain a gelator solution; contacting the gelator solution with spilled oil on a surface to obtain a gel comprising the oil on the surface, wherein the spilled oil is selected from the group of synthetic oil, natural oil, crude oil, fuel oil, petroleum fractions, combinations thereof; gathering the gel from surface; heating the gel to a temperature in the range of 50-150° C. to obtain the oil and to reclaim the compound of Formula I.

In one implementation, the present disclosure relates to a process of containing oil spillage, said process comprising the steps of: contacting a compound of Formula II with an aromatic solvent at a temperature in the range of 40-90° C. to obtain a gelator solution; contacting the gelator solution with spilled oil on a surface to obtain a gel comprising the oil on the surface, wherein the spilled oil is selected from the group of synthetic oil, natural oil, crude oil, fuel oil, petroleum fractions, combinations thereof; gathering the gel from surface; heating the gel to a temperature in the range of 50-150° C. to obtain the oil and to reclaim the compound of Formula II. The surface can be land surface, sea water surface, or fresh water surface.

EXAMPLES

The disclosure will now be illustrated with working examples, which is intended to illustrate the working of disclosure and not intended to take restrictively to imply any limitations on the scope of the present disclosure. Other examples are also possible which are within the scope of the present disclosure.

Example 1

Separation of Oil Spillage from Sea/Water Bodies

The gelator of Formula II was mixed with toluene at a ratio of 10 gm of gelator per 100 gm of the solvent and at a temperature of approximately 60 deg C. to form a homogeneous solution in a drum which may be of 0.5-3 m diameter and TL-TL (tangent to tangent/height) of 1-7 m. The solution was then sprayed with a specialised spray nozzles at a spraying velocity of 2-20 m/sec over the oil spill on sea water surface under laboratory conditions. The spray nozzle in this case was a tubular pipe of CS or SS316 of 1 inch-8 inches in diameter, and having 6-20 perforations arranged in series. The holes were varied from ¼ inch to 2 inch in size and the series of holes or perforations were 90-270 deg apart. The gelator solution was sprayed until crude oil was observed on the water surface. The gelator solution along with the crude oil results in the formation of gel which could be easily separated from water. The gelated hydrocarbon was easily recovered from the gel including the amphiphilic gelators by heating the gel to a temperature of 120 deg C. in a heating tank preferably by electrical heating.

The separated oil were then decanted/routed from the bottom of the tank/drum. The gel can be reused for further treatment.

This application was tested for removing kerosene/diesel as well as different types of crude spill from water bodies.

The gelator of Formula II when dissolved in methanol and acetone did not show gelling property with crude oil and other distillates.

Example 2

Separation and Recovery of Oil in Refinery ETP

The gelator can be used in this application of oil removal from effluent. The gelator of Formula II was first mixed with toluene at 40-50 deg C. to form a homogeneous solution in a drum (capacity 1-10 m$^3$) and then sprayed via nozzle over the first Oil Catcher tank (6.0 m×3.5 m×3.6 m) with the help of specialized spraying nozzle at a velocity of 2-20 m/sec. The spraying nozzle was a single pipe of 1-8 inch diameter with ¼ inch holes arranged at 45-270 deg apart. The residence time for effective removal of the floating hydrocarbon components which includes both crude oil as well as distillates was calculated as 10-60 min depending on the composition of the hydrocarbon. The gel layer comprising crude oil selectively restricted the flow of organic phase in preference to water from a biphasic mixture of oil and water and formed a rigid gelated layer which can be easily separated. The rigid gelated hydrocarbon layer was then skimmed off by the existing rake and sent for recycle to a tank with jacketed electrical heating provision to heat to 70 deg C. The loading capacity of the Electrical Heater may vary from 2-20 kW. The tank as well as the other piping and fittings may be made of CS or SS304 as required while the sumps may be RCC sump.

It was observed that the gel exhibits minimum gelation ability with crude oil that may be attributed to its complex composition having a mixture of thousands of hydrocarbons as well as of inorganic impurities. However the gel formation observed with crude oil was stable for at least one month without showing any degradation over time.

The above application also eliminates the process of incorporating multiple oil catcher in a Refinery ETP Plant apart from efficient separation of hydrocarbons from aqueous phase. With the application of gel the size reduction of equipment can be achieved in a ETP Plant apart from process improvement or intensification.

Example 3

Separation of Water From Crude Oil In Day Tanks Using Gel

The salt of gelator of Formula II selectively form the rigid structure with water instead of the hydrocarbon phase.

The hot polar gelator solution was prepared by mixing 1 wt % of the compound of Formula II with water and equivalent amount of NaOH and the solution was heated to 60 deg C. The polar gelator solution was sprayed in the oil recovery drum (of 10-200 m$^3$ capacity) having oil and water interface. The polar gelator solution was sprayed through the liquid spray nozzle designed to restrict the pressure drop up to 0.5-2.0 bar and operating at a spraying velocity of 2-50 m/sec. The gelation solution was then stirred continuously with agitator/rake/impeller operating at 100-500 rpm rotational speed and then allowed to settle in the tank. The residence time was approximately 1-4 hour. After 1-2 hr or so, it was observed that the gelated solution absorbs the aqueous compounds and eventually the entire water content from the crude oil/petroleum fraction layer was gelated in a continuous phase, keeping the aqueous layer intact in the liquid state below leaving the oil or the hydrocarbon phase floating at the top. The crude /oil layer which collected above the gel was routed out from the tank by monitoring closely with interface level transmitters.

However, if the crude oil quantity is limited compared to the aqueous phase, hydrophobic based dipeptide-low molecular organo-gelator, i.e., compound of Formula II was used for separation. In such case the gelator forms the rigid structure with the crude oil or hydrocarbon phase leaving the aqueous phase to settle at the bottom. Then the bottom outlet valve of the Oil Recovery Drum was slowly opened to drain out the aqueous liquid from the drum. The level of the aqueous phase was monitored with the help of interface level transmitters. On completion of draining of water, the gel that was formed was transferred by a vacuum pump.

The gelator including the hydrophobic material, i.e., crude oil was then heated by jacket heater/immersion heater in the regeneration drum where operating temperature is of the range of 60-80 deg C.

On heating the absorbed hydrocarbon gel, the absorbed oil is separated from the gel. The crude oil settle at the bottom of the drum and the gel floats on the surface. The oil was slowly decanted and gel was collected on the sieve plate located at the bottom of the regeneration drum. The sieve plate was scrapped off mechanically from the manhole or hand hole.

The recovered gel can be reused or recycled retained 99% of its hydrocarbon absorbing capacity. The crude oil was then routed to storage tanks.

Example 4

Sludge Treatment Process

Sludge deposited in crude tanks limits the capacity of crude tanks. The sludge was transferred from the crude tanks with the help of hot kerosene as the transferring medium to a separate drum at a pumping rate of 2-500 m$^3$/hr from atmospheric storage tanks having holding capacity of 20-1000 m$^3$. Similar to the processes explained in the above examples, gelated solution was prepared in a potable drum of 5-50 m$^3$ capacity with hot toluene and compound of Formula II and the solution prepared was sprayed over the sludge at a velocity of 5-10 m/sec.

Initially the hot gelator solution and the diluted sludge was thoroughly mixed by stirring with a rake or impeller operating at a tip velocity of 1-10 m/sec. The impeller design was pitched blade turbine type or disk mounted type to promote axial flow. However impeller designs such as hub or disk mounted with flat or curved blade to provide shearing action and enhanced liquid-liquid interfacial areas are preferred. While mixing the stirring rate was varied from 200-1000 rpm with impeller tip velocity of 1-10 m/sec. Also, the impeller may be of larger size impeller blades or may be hub or disk mounted with curved blades to promote higher circulation rates. The gelator application for treating sludge requires rigorous mixing or agitation.

The mixed solution was then allowed to settle by providing residence time of 1-2 hour, as the gelated solution has the potential for selective extraction of oil from the sludge leaving aside the clay, minerals and other particles of the sludge which settle at the bottom of the Drum/Tank. The thoroughly mixed solution slowly formed a continuous layer while the sludge settled at the bottom of the cone, as designed in the oil separation drum.

The hot oil and gelator solution was then slowly transferred to the regeneration drum while it was hot and its fluidity maintained to flow via pump. It was then cooled by circulating cooling water through the jacket of the regeneration drum. The process may require hot kerosene to maintain the fluidity inside the drum while mixing or transferring. The cooled gelated oil is again heated to separate the gel form the absorbed oil.

In a different process for recovery of oil from sludge, the gelated -oil was allowed to settle and rigidify in the oil separation tank itself, by cutting of the electrical jacket heating of the oil separation drum. The oil-gel slowly solidified after 2-4 hrs, and the layer was skimmed off from the top of the sludge particles that settle at the bottom. The gelated crude oil was then routed to a regeneration drum or heating tank for recovering the crude oil, termed as recovery drum by heating to a higher temperature of 65-80 deg C. The sludge which consists of dirt particles, salts, clay sand and mud settled on the perforated plate or sieve plate with 500 micron-0.5 mm size holes which is located in the drum.

The schemes requires a very effective electric heating system in the drums with resistance wiring which is made of the usual coiled form with threaded beads to operate by heat radiation. The radiation heater thermally heats a fluid contained by Tank to a desired temperature 60-120 deg C. The heating element may be either immersed inside the Drum/Tank or wounded around the tank.

The sludge was flushed off from the tank with hot kerosene at a circulating rate lesser than 2-100 m$^3$/hr.
Advantages gained in the example illustrative process in this subject matter:

The process disclosed herein is supported by the excellent gelation ability exhibited by gel solution in which the organic compounds are meshed to form a rigid or semi-rigid mixture. The feed stream or the treating stream of the processes developed may be different types of crude oils including naphthenic or high sulphur crudes, with different refinery distillates as well as with a number of aliphatic and aromatic organic solvents which proves the gelation ability exhibited by peptide amphiphilic organo-gelator. The gelation ability is not only limited to monophasic oils but phase selective gelation of oil in a mixture of oil and water/sea water is equally possible invoking potential applications in oil spillage/recovery and sludge treatment in refinery or oil well sites.

The process is attractive in the sense that it is simple, compact and requires minimum utilities which would in turn favor low capital and operating cost for installation and operation. The processes developed may operate in batch mode as well in continuous mode and the entire plant may be skid mounted modular unit. Hence it offers significant advantages with respect to investment costs and energy consumption and space/plot plan required for installation. The gelator application lead to development and design of complete process plant that would result in better product qualities and higher yields.

The process finds utility in the following sectors:
In Chemical Laboratories—To contain the oil or solvent spill. To contain the water spill where water is detrimental such as in pharma industries.
In hotels/restaurants—To contain the oil spillage.
Petrochemical/Polymer Industries where efficient water separation is a pre requisite before operating in cryogenic conditions.

Oil wells and oil fields where interphase separation is critical. ETP where the treated effluent stream is disposed into sea water with oil spill over.

Although the subject matter has been described in considerable detail with reference to certain examples and implementations thereof, other implementations are possible. As such, the spirit and scope of the appended claims should not be limited to the description of the preferred examples and implementations contained therein.

We claim:

1. A process for separating a hydrophobic material from a mixture of hydrophobic and hydrophilic material, said process comprising the steps of:
   a. contacting a compound of Formula I:

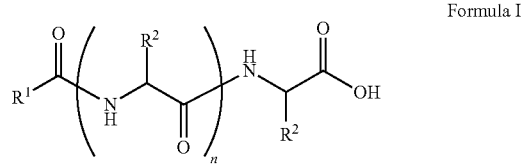

Formula I wherein, $R^1$ substituted or unsubstituted $C_{10}$ to $C_{25}$ alkyl; $R^2$ is $C_1$ to $C_{10}$ alkyl substituted with a heteroatom selected from O, N and S, wherein the heteroatom is substituted with $C_1$ to $C_3$ alkyl; n is 1 to 3, with an aromatic solvent at a temperature in the range of 40–90° C. to obtain a gelator solution;
   b. contacting the gelator solution with a mixture of hydrophobic and hydrophilic material to obtain a gel comprising the hydrophobic material and a residue of hydrophilic material;
   c. separating the gel from the residue of hydrophilic material;
   d. heating the gel to a temperature in the range of 50–150° C. to obtain the hydrophobic material and to reclaim the compound of Formula I.

2. The process for separating a hydrophobic material from a mixture of hydrophobic and hydrophilic material as claimed in claim 1, wherein the hydrophobic material is a hydrocarbon.

3. The process for separating a hydrophobic material from a mixture of hydrophobic and hydrophilic material as claimed in claim 1, wherein the hydrophobic material is oil selected from the group of synthetic oil, natural oil, crude oil, fuel oil, petroleum fractions, combinations thereof.

4. The process for separating a hydrophobic material from a mixture of hydrophobic and hydrophilic material as claimed in claim 1, wherein the hydrophilic material is selected from the group consisting of water, polar solvents, sludge, and combinations thereof.

5. The process for separating a hydrophobic material from a mixture of hydrophobic and hydrophilic material as claimed in claim 1, wherein the aromatic solvent is selected from the group consisting of toluene, xylene, ethylbenzene, petroleum fractions, and combinations thereof.

6. The process for separating a hydrophobic material from a mixture of hydrophobic and hydrophilic material as claimed in claim 1, wherein the compound of Formula I weight % in the gelator solution is in the range of 0.1–20%.

7. The process for separating a hydrophobic material from a mixture of hydrophobic and hydrophilic material as claimed in claim 1, wherein the mixture of hydrophobic and hydrophilic material is a biphasic mixture, wherein the biphasic mixture comprises of oil selected from the group of synthetic oil, natural oil, crude oil, fuel oil, petroleum fractions, and combinations thereof and water.

8. The process for separating a hydrophobic material from a mixture of hydrophobic and hydrophilic material as claimed in claim 1, wherein the mixture of hydrophobic and hydrophilic material is a triphasic mixture, wherein the triphasic mixture comprises of oil selected from the group of synthetic oil, natural oil, crude oil, fuel oil, petroleum fractions, combinations thereof, water, and sludge.

9. A process for separating a hydrophobic material from a mixture of hydrophobic and hydrophilic material, said process comprising the steps of:
   a. contacting a compound of formula I:

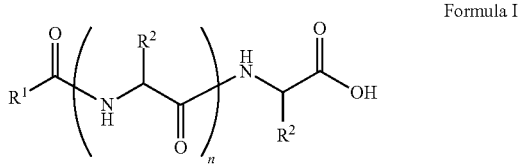

Formula I wherein, $R^1$ is substituted or unsubstituted $C_{10}$ to $C_{25}$ alkyl; $R^2$ is $C_1$ to $C_{10}$ alkyl substituted with a heteroatom selected from O, N and S, wherein the heteroatom is substituted with $C_1$ to $C_3$ alkyl; n is 1 to 3, with a base and a hydrophilic solvent at a temperature in the range of 40–90° C. to obtain a polar gelator solution;
   b. contacting the polar gelator solution with a mixture of hydrophobic and hydrophilic material to obtain a gel comprising the hydrophilic material and a residue of hydrophobic material;
   c. separating the residue of hydrophobic material from the gel to obtain the hydrophobic material; and
   d. heating the gel to a temperature in the range of 50-100° C. to reclaim the compound of Formula I.

10. The process for separating a hydrophobic material from a mixture of hydrophobic and hydrophilic material as claimed in claim 9, wherein the hydrophobic material is a hydrocarbon.

11. The process for separating a hydrophobic material from a mixture of hydrophobic and hydrophilic material as claimed in claim 9, wherein the hydrophobic material is oil selected from the group of synthetic oil, natural oil, crude oil, fuel oil, petroleum fractions, combinations thereof.

12. The process for separating a hydrophobic material from a mixture of hydrophobic and hydrophilic material as claimed in claim 9, wherein the hydrophilic material is selected from the group consisting of water, polar solvents, sludge, and combinations thereof.

13. The process for separating a hydrophobic material from a mixture of hydrophobic and hydrophilic material as claimed in claim 9, wherein the base is selected from the group consisting of sodium hydroxide, potassium hydroxide, and combinations thereof.

14. The process for separating a hydrophobic material from a mixture of hydrophobic and hydrophilic material as claimed in claim 9, wherein the compound of Formula I weight % in the polar gelator solution is in the range of 0.1-20%.

15. The process for separating a hydrophobic material from a mixture of hydrophobic and hydrophilic material as claimed in claim 9, wherein the mixture of hydrophobic and hydrophilic material is a biphasic mixture, wherein the biphasic mixture comprises of oil and water.

16. A process for separating an oil from a mixture of oil and water, said process comprising the steps of:
   a. contacting a compound of formula I:

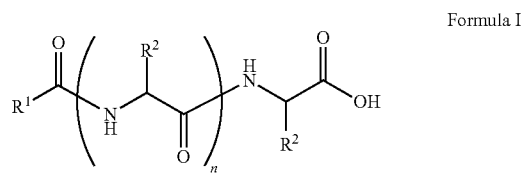

Formula I wherein, $R^1$ is substituted or unsubstituted $C_{10}$ to $C_{25}$ alkyl; $R^2$ is $C_1$ to $C_{10}$ alkyl substituted with a heteroatom selected from O, N and S, wherein the heteroatom is substituted with a $C_1$ to $C_3$ alkyl; n is 1 to 3, with toluene in a weight ratio of 1:99 at a temperature in the range of 40-90° C. to obtain a gelator solution;
   b. contacting the gelator solution with a mixture of oil and water to obtain a gel and a residue of aqueous material;
   c. separating the gel from the residue of aqueous material; and
   d. heating the gel to a temperature in the range of 50-150° C. to obtain oil and to reclaim the compound of Formula I.

17. A process for separating an oil from a mixture of oil, water, and sludge, said process comprising the steps of:
   a. contacting a compound of formula I:

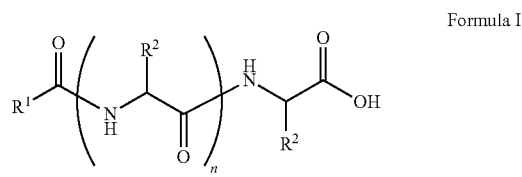

Formula I wherein,
   $R^1$ is substituted or unsubstituted $C_{10}$ to $C_{25}$ alkyl; $R^2$ is $C_1$ to $C_{10}$ alkyl substituted with a heteroatom selected from O, N and S, wherein the heteroatom is substituted with a $C_1$ to $C_3$ alkyl; n is 1 to 3, with toluene in a weight ratio of 1:99 at a temperature in the range of 40-90° C. to obtain a gelator solution;
   b. contacting the gelator solution with a mixture of oil, water, and sludge to obtain a gel and a residue of aqueous material;
   c. separating the gel from the residue of aqueous material; and
   d. heating the gel to a temperature in the range of 50-150° C. to obtain oil and the gelator solution and to reclaim the compound of Formula I.

18. A process for separating oil from a mixture of oil and water, said process comprising the steps of:
   a. contacting a compound of formula I:

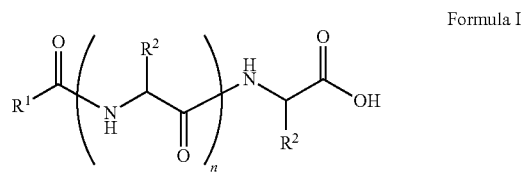

Formula I wherein,

R$^1$ is substituted or unsubstituted C$_{10}$ to C$_{25}$ alkyl; R$^2$ is C$_1$ to C$_{10}$ alkyl substituted with a heteroatom selected from O, N and S, wherein the heteroatom is substituted with a C$_1$ to C$_3$ alkyl; n is 1 to 3, with sodium hydroxide and water at a temperature in the range of 40-90° C. to obtain a polar gelator solution;

b. contacting the polar gelator solution with a mixture of oil and water to obtain a gel and a residue of oil;

c. separating the residue of oil from the gel to obtain the oil; and d. heating the gel to a temperature in the range of 50-150° C. to reclaim the compound of Formula I.

19. A process of containing oil spillage, said process comprising the steps of:

a. contacting a compound of Formula I:

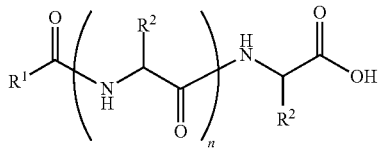

Formula I wherein, R$^1$ is substituted or unsubstituted C$_{10}$ to C$_{25}$ alkyl; R$^2$ is C$_1$ to C$_{10}$ alkyl substituted with a heteroatom selected from O, N and S, wherein the heteroatom is substituted with a C$_1$ to C$_3$ alkyl; n is 1 to 3, with an aromatic solvent at a temperature in the range of 40-90° C. to obtain a gelator solution;

b. contacting the gelator solution with spilled oil on a surface to obtain a gel comprising the oil on the surface, wherein the spilled oil is selected from the group of synthetic oil, natural oil, crude oil, fuel oil, petroleum fractions, combinations thereof;

c. gathering the gel from surface;

d. heating the gel to a temperature in the range of 50-150° C. to obtain the oil and to reclaim the compound of Formula I.

20. The process as claimed in 19, wherein the surface is land surface, sea water surface, or fresh water surface.

* * * * *